United States Patent [19]
Beavers et al.

[11] Patent Number: 5,571,955
[45] Date of Patent: Nov. 5, 1996

[54] MONITORING OF STRESS CORROSION CRACKING

[75] Inventors: John A. Beavers, Columbus; Neil G. Thompson, Dublin, both of Ohio

[73] Assignee: CC Technologies Systems, Inc., Columbus, Ohio

[21] Appl. No.: 418,015

[22] Filed: Apr. 6, 1995

[51] Int. Cl.⁶ .............................. G01N 17/04; G01N 3/10
[52] U.S. Cl. .................................... 73/86; 73/799; 422/53
[58] Field of Search ........................... 73/86, 866, 866.5, 73/799; 436/6; 422/53; 324/71.2

[56] References Cited

U.S. PATENT DOCUMENTS

| | | | |
|---|---|---|---|
| 4,020,696 | 5/1977 | Vrolyk | 73/86 X |
| 4,389,880 | 6/1983 | Robinet | 73/86 |

FOREIGN PATENT DOCUMENTS

| | | | |
|---|---|---|---|
| 0065137 | 5/1980 | Japan | 436/6 |

OTHER PUBLICATIONS

Mars G. Fontana, Corrosion Engineering, Third Edition, McGraw-Hill, New York, 1986, pp. 109–142.

*Primary Examiner*—Michael Brock
*Attorney, Agent, or Firm*—Frank H. Foster; Kremblas, Foster, Millard & Pollick

[57] ABSTRACT

A corrosion monitoring apparatus and method for determining the corrosive effects of a chemical environment, having an environmental pressure, on a vessel containing the chemical environment. A probe is exposed to the environment and is made of a material substantially similar to that of which the vessel is made. The probe has a sealed internal chamber which contains a pressurized fluid which is monitored. A pressure transducer is in communication with the sealed internal chamber of the first probe for translating any pressure change within the chamber into a (preferably electrical) signal which is indicated by an electrical meter or similar device. Stress corrosion cracking of the probe causes fluid leakage and, therefore, a pressure change.

15 Claims, 1 Drawing Sheet

MONITORING OF STRESS CORROSION CRACKING

TECHNICAL FIELD

This invention relates to a method and an apparatus for monitoring metal corrosion in a chemical environment, and more specifically relates to monitoring stress corrosion cracking (SCC) of a selected material being utilized in a specific chemical environment.

BACKGROUND ART

The corrosion of metals occurs in many forms when metals react with their environments. There are many devices for measuring some types of corrosion for predicting or preventing the failure of a selected component. However, one form of corrosion for which there is no known monitoring device is SCC. Stress corrosion cracking refers to intergranular or intragranular cracking caused by the simultaneous presence of tensile stress and a specific corrosive medium. A specific chemical environment must exist in which a susceptible material has a tensile stress applied to it in order for this type of corrosion to occur. Under these conditions, a material that is otherwise corrosion resistant, will fail in a brittle fashion. For example, stainless steel will fracture in a short amount of time if a sufficient tensile stress is applied to it while it is exposed to a hot concentrated chloride environment. Stress corrosion cracking is described in Mars G. Fontana, *CORROSION ENGINEERING*, Third Edition, McGraw-Hill, New York, 1986, pp. 109-142.

Although there are no known devices made for monitoring SCC, an existing device made for measuring electrochemical noise (indicating pitting corrosion) has been suggested as capable of measuring SCC. This device includes a pair of electrodes spaced a small distance apart in a chemical environment. When pitting occurs, the voltage measured between the electrodes changes slightly, yet abruptly. This voltage change qualitatively represents the occurrence of pitting. It has been claimed that this device could work for monitoring SCC, but this claim has not been proved and is viewed with some doubt.

Therefore, the need exists for a device for monitoring the SCC of a selected material exposed to a specific chemical environment.

BRIEF DISCLOSURE OF INVENTION

The invention contemplates an apparatus for monitoring corrosion of a material exposed to a chemical environment. The apparatus comprises a first probe exposed to the chemical environment wherein the probe is made of a material substantially similar to the first material. Furthermore, the probe has a sealed internal chamber containing a pressurized fluid. A pressure transducer is positioned in communication with the sealed internal chamber of the first probe so that a change in pressure within the internal chamber can be detected to indicate corrosion of the probe.

The invention also contemplates a method of monitoring the corrosion of a first material exposed to a chemical environment having an environmental pressure. The method comprises pressurizing a fluid, which is contained in a sealed internal chamber of a first probe, to a specific fluid pressure. The probe is made of a material substantially similar to the first material. A pressure transducer is preferably connected in communication with the chamber of the first probe and the first probe is exposed to said environment. The pressure detected by the transducer is then monitored. A decrease in pressure indicates corrosion.

Figure 1:
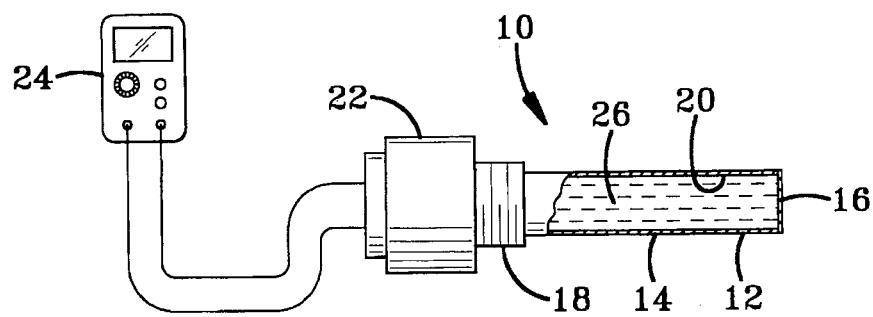
FIG. 1 is a side view in section illustrating the preferred monitoring apparatus.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

The invention contemplates an apparatus for monitoring SCC of a stressed material exposed to a chemical environment. The apparatus consists of two probes. Both probes are cylindrical in shape and contain chambers that are sealed from the external environment. They are fabricated of the metallic material to be monitored. The internal chambers of the probes are filled with a non-corrosive fluid or gas and pressurized to achieve the desired hoop stress in the wall of the probe. The probes are placed in the potentially corrosive environment (typically a vessel or pipe containing a liquid) and communicate with a pressure transducer by means of a sealed corrosion resistant metallic tube. The pressure transducer is located external to the vessel or pipe in a convenient location for monitoring.

One of the two probes is pressurized to achieve a high stress, with respect to the yield stress of the metal, in the wall of the probe. The second probe is pressurized only high enough to allow for monitoring purposes. Where the external environment is pressurized, the pressure of both probes must be increased to compensate for this pressure. The pressure of the probes is monitored as a function of time. A drop in the pressure of only the high pressure probe indicates that the conditions in the environment are conducive to SCC. A drop in pressure of both probes indicates that the conditions in the environment are conducive to pitting corrosion.

Two applications are now planned for the probe: a waste tank for disposal of high level nuclear waste and a paper machine. The waste tanks are approximately one (1) million gallons in volume and are buried about fifty (50) feet deep. They are fabricated of ASTM Grade A 516 steel. The user wishes to monitor for SCC susceptibility at various depths in the tank. The working end of the probe will be about six (6) inches long and individual probes will be placed at the different depths. Each probe will be connected to a long tube that is fabricated such that it is resistant to SCC either because of a reduced stress (thicker wall) or a more cracking resistant material. The pressure transducers will be located within a pit on top of the tanks. The electrical signals from the transducers will be sent to a computer data acquisition system.

The second application is a paper machine in a pulp and paper plant. The probes will have male pipe threads on one end (as shown in the figure) and also will be about six (6)

inches long. The probes will be inserted in threaded holes in the walls of piping and vessels in the plant. Typically, these probes will be made of a stainless steel. The pressure transducers may be connected very close to the probe or may be installed in a more convenient location with a pressure tube connecting the probe and the transducer.

The preferred apparatus illustrated in FIG. 1 shows a probe 10 made of a cylindrical tube 12 having sidewall 14. Ends 16 and 18 are rigidly attached to the tube 12, preferably by welding, forming a sealed, enclosed chamber 20 within the boundaries of the sidewall 14 and the ends 16 and 18.

A pressure transducer 22 attaches to and extends through the end 18, so the transducer 22 is in communication with the internal chamber 20. The transducer 22 preferably generates an electrical signal when there is a change of pressure in the chamber 20. However, the transducer 22 can be any device which senses a change in the pressure within the chamber 20 and indicates the pressure change. For example, the transducer could be a conventional bellows attached to a needle on a scale, the scale indicating the degree of pressure change. The signal from the preferred transducer can be indicated to a person observing by, for example, a meter 24. The intensity of the electrical signal generated by transducer 22 is preferably proportional to the pressure change. An example of one such transducer is an Omega Engineering, Inc. Model Number PX902 (0–5000 pounds per square inch gauge) with a DP205-S meter.

A fluid 26, preferably a liquid, is contained within the chamber 20. The preference for a liquid is due to safety factors including the small amount of volume change in the liquid upon fracture of the probe and release of the liquid. Since most liquids are nearly incompressible, the liquid will not attain a significantly greater volume when released than when pressurized. A compressed gas could, on the other hand, expand greatly, creating safety hazards. However, as an alternative embodiment, the fluid 26 may be a gas, and an inert gas is preferred among gases to avoid contaminating any chemical environment to which the probe 10 is exposed.

In the preferred embodiment of the present invention, the probe 10 is exposed to a chemical environment contained within a vessel, such as a storage tank or a pipe, having an environmental pressure.

The term "chemical environment" is meant to include the environment to which the probe 10 is exposed, including chemical substances contained within a vessel in which the probe is inserted which have a chemical effect on the vessel and the probe. The chemical environment also includes any electrical effect (e.g. galvanic corrosion) and any hydraulic effect (e.g. tensile stress).

The pressure within a vessel in which the probe is inserted is referred to as the "environmental pressure". This term is meant to indicate the pressure within the vessel causing a tensile stress on the vessel which may cause stress corrosion cracking. It is to be emphasized that the term "environmental pressure" is not meant to be implied as an equivalent to atmospheric pressure. It is possible that the environmental pressure within a vessel may at times equal the atmospheric pressure, but in that case stress corrosion cracking is less likely since there will be no applied tensile stress on the vessel. Residual stresses may be present due to fabrication (welding & forming).

The purpose of exposing the probe to the chemical environment of the vessel is to simulate and therefore predict the corrosion of the vessel by monitoring the corrosion of the probe. The probe 10 simulates, or represents an accelerated simulation of, vessel corrosion to give an early warning of possible corrosion failure of the vessel. In order that the probe 10 accurately simulates the corrosion of the vessel, it is desirable that the probe 10 be made of material substantially similar to that of which the vessel is made. Furthermore, other parameters such as internal probe pressure (which applies a tensile stress), sidewall and end thicknesses, etc., affect the time required for corrosion fracture to occur. These parameters can be changed to make corrosion of the probe 10 accurately simulate the corrosion of the vessel, and provide an early warning of a possible vessel fracture. Changing the parameters such as internal pressure and probe thicknesses includes decreasing sidewall and end thicknesses and increasing internal probe pressure in order to decrease the amount of time required for probe fracture. Greater thicknesses and decreased pressure will increase the amount of time it takes for the probe to fracture under stress corrosion cracking. For example, the probe sidewall 14 may have a thickness of 10–30 mil (1/100 to 1/10) of the thickness of the wall of the vessel into which it is inserted) and the pressure in chamber 20 may be 4,000 p.s.i. resulting in a tensile stress of 70%–80% of the Yield Stress of the probe sidewall 14.

Figure 2:
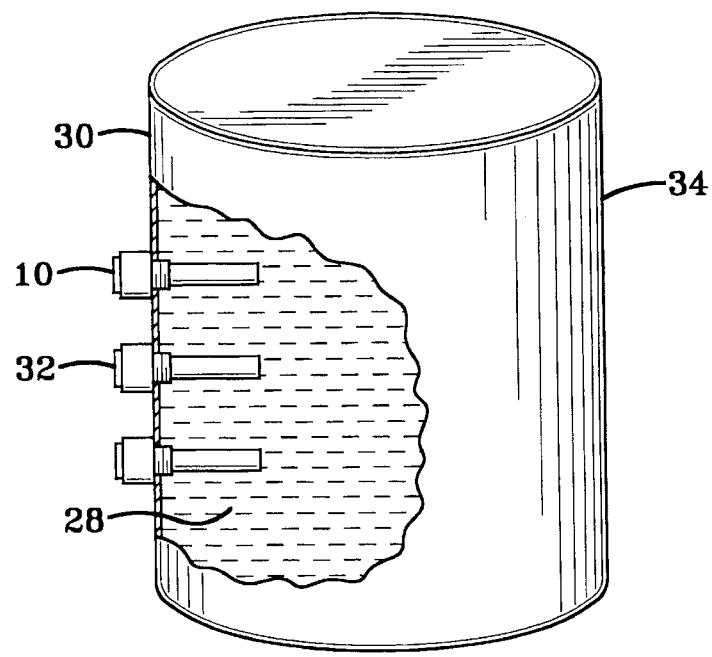
FIG. 2 is a side view in section illustrating a pair of the preferred monitoring probes in an operable position on a tank.

FIG. 2 shows a tank 34 which is a typical, pressurized vessel used in chemical industries for containing a fluid 28, usually a liquid (e.g. high level nuclear waste). The probe 10 is, in its operable position, inserted through a wall 30 and into the interior of the tank 34 exposing a large portion of the outer surface of the probe 10 to the fluid 28.

Once the probe 10 is inserted through the tank wall 30, a monitoring device such as the meter 24 shown in FIG. 1 is connected to the transducer 22 to indicate any change in the pressure of the fluid 26 contained within the probe 10. A monitoring device, such as the meter 24, serves the purpose of monitoring the pressure within the chamber 20 of the probe 10 and signals or records data of a substantial change in that pressure. A monitor could, of course, include a person watching for a specific pressure change indicated by a meter, or an alarm which sounds upon the occurrence of a pressure change above a specified threshold. Therefore, monitoring includes a machine which senses pressure changes and indicates them in some way.

The fluid 26 contained within the chamber 20 of the probe 10 has been pressurized to a fluid pressure substantially greater than the pressure of the fluid 28 within the tank 34. The pressure of the fluid 26 causes a tensile stress to be applied to the probe sidewall 14. The tensile stress, combined with exposure to the same chemical environment to which the tank 34 is exposed, will cause the probe 10 to stress corrode at a similar rate or a greater rate than the tank 34 depending upon whether simulation or accelerated corrosion is being tested.

When the effects of stress corrosion cracking begin to develop, small cracks will form in the sidewalls 14 or the end 16 of probe 10, and some of the fluid 26 will leak out of the cracks. This leaking out of the fluid 26 will cause a decrease in pressure within the chamber 20. The preferred transducer 22 will generate an electrical signal proportional to this change in pressure which the meter 24 will register.

Although the probe 10 is preferably made of the same material as the tank 34, the probe 10 and the tank 34 need not be made of exactly the same material chemically and metallurgically. However, the closer the materials are in susceptibility to stress corrosion cracking, the better the probe 10 will represent the tank 34, and therefore the better the probe 10 will indicate stress corrosion cracking occurring in the tank 34. If, for example, the tank 34 is made of type 304 stainless steel, then the probe 10 will also be made of type 304 stainless steel. If the fluid 28 is boiling magnesium chloride, then the probe 10 and the tank 34 will very likely be susceptible to stress corrosion cracking, and the probe 10 will warn of the failure of the tank 34 before tank 34 failure occurs.

In the preferred embodiment, a second probe 32 is inserted into the tank 34 similarly to the first probe 10. The second probe 32 has physical properties and geometric dimensions virtually identical to the first probe 10. The chamber (not shown) within the second probe 32 also contains a fluid, but the fluid is pressurized to a pressure substantially lower than the pressure of the fluid 26 within the first probe 10, and slightly greater than the pressure of the fluid 28 within the tank 34. This second probe 32 is a "control" for indicating whether the changing pressure within the first probe 10 is caused by stress corrosion cracking or some other type of corrosion such as pitting or general corrosion. Because the second probe 32 is pressurized just slightly greater than the pressure of the fluid 28 in tank 34, a change in the pressure in probe 32 caused by a leak of the probe 32 will still be registered on a transducer in a manner substantially identical to the transducer 22 communicating with the fluid within the first probe 10. However, failure of the second probe 32 will most likely not be due to stress corrosion cracking since probe 32 has no appreciable applied tensile stress which is one of the three elements required for stress corrosion cracking to occur. If the second probe 32 and the first probe 10 fail at approximately the same time, this will indicate a failure caused by something other than stress corrosion cracking. This second probe 32 can be a valuable tool for measuring corrosion rates of other forms of corrosion.

Therefore, the fluid pressure within the probe of the preferred embodiment is determined by the purpose of the monitoring experiment. For example, if the probe is being used to determine the actual rate of stress corrosion of the vessel in which it is inserted, then the pressure within the probe should be only as high as is necessary to apply a tensile stress to the probe wall similar to that applied to the vessel, and also to register a change in pressure upon cracking of the probe. However, if the purpose of the monitoring is to provide an accelerated representation of the effect of the chemical environment and the environmental pressure on the vessel, then the probe should be pressurized to a substantially higher pressure to apply a higher tensile stress to the probe wall than is applied to the vessel wall. This substantial difference in pressure will increase the effect of stress corrosion cracking, thereby giving an earlier warning of possible vessel failure.

Figure 3:
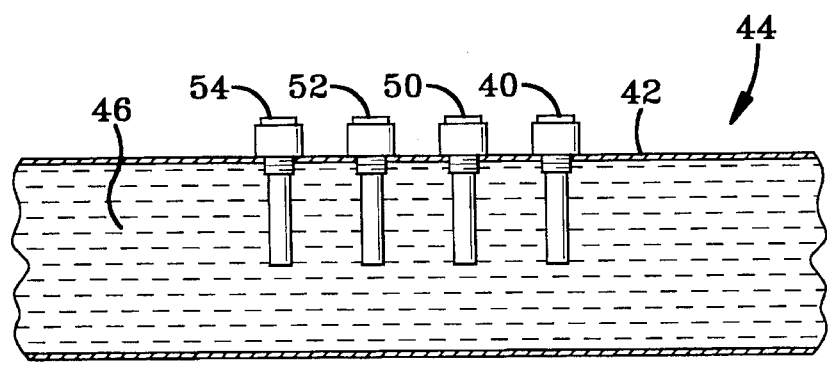
FIG. 3 is a side view in section illustrating the preferred monitoring probe in an operable position on a pipe.

As an alternative to the preferred embodiment, a plurality of probes 40, 50, 52 and 54 (shown in FIG. 3) may be inserted into a vessel such as pipe 44 having a specific chemical environment and a specific environmental pressure. Each of these probes 40, 50, 52 and 54 has geometric characteristics different from each other, but all are similar to the preferred probe 10 inasmuch as they all have an internal chamber containing a pressurized fluid in communication with a transducer. The fluid pressure within each probe may also differ from the other probes. The purpose of this alternative embodiment is to provide a plurality of probes having characteristics spread over a spectrum, the spectrum representing the susceptibility of the probes to stress corrosion cracking.

As an example of this spectrum of susceptibility, each probe 40, 50, 52 and 54 may have successively thinner sidewalls, and/or successively higher pressures within them so as to make the probes successively more susceptible to stress corrosion cracking. Each of the four probes has a transducer, as in the preferred embodiment, which signals a change in the internal pressure. All of the transducers are connected to a central data collection device, such as a computer, which records any change in pressure in any of the probes. Using this apparatus, a more quantitative measurement of the effects of stress corrosion cracking on the vessel can be obtained, such as the rate of stress corrosion cracking. The result of such an apparatus is probe fractures at time intervals which can be extrapolated to a time at which the vessel containing the chemical environment will most likely fracture. The likelihood of fracture can be predicted by relating the pressures within the probes and the sidewall thicknesses to the pressure within the vessel and the vessel wall thicknesses.

Because the fracture of a probe inserted in the wall of a vessel will allow the contents of the vessel to eventually flow into the probe (once the internal pressure of the probe equalizes with the pressure within the vessel), it is desirable that a leak prevention means be installed in the probe. A check valve or other similar device can be attached at the transducer of the probe to prevent fluid from flowing out of the probe via any passageway formed for the transducer. Alternatively, if the probe is normally installed in a vessel with some portion of the probe extending out of the vessel, then a one-way valve in the portion of the probe that remains outside the vessel (i.e. the portion that is not subject to the chemical environment of the vessel) would prevent the flow of fluid from the fractured portion of the probe into the end of the probe extending out of the vessel. This would also protect the transducer from the chemical environment.

In describing the present invention, the term transducer is used to describe a device which transforms a change in hydraulic pressure within a probe into a signal which is perceivable by humans, either in its original form such as the movement of a mechanical pressure metering device, or after further transformations, such as by electrical circuitry. However, the term transducer also includes other devices such as a strain gauge which can be used to detect pressure.

While certain preferred embodiments of the present invention have been disclosed in detail, it is to be understood that various modifications may be adopted without departing from the spirit of the invention or scope of the following claims.

We claim:

1. An apparatus for monitoring corrosion of a first material exposed to a chemical environment having an environmental pressure, the apparatus comprising:

(a) a first probe exposed to said environment, the probe being made of a material substantially similar to the first material, and having a sealed internal chamber containing a pressurized fluid;

(b) a second probe exposed to said environment, the probe being made of a material substantially similar to the first material, and having a sealed internal chamber containing a pressurized fluid, wherein the fluid is pressurized to a fluid pressure different than the fluid pressure in the first probe; and (c) a pressure transducer in communication with at least one of the sealed internal chambers.

2. An apparatus in accordance with claim 1, wherein the fluid pressure in the first probe chamber is substantially higher than said environmental pressure.

3. An apparatus in accordance with claim 2 further comprising an indicator, connected to the transducer, for indicating when a change in the fluid pressure in an internal chamber has occurred.

4. An apparatus in accordance with claim 3 further comprising a plurality of probes substantially similar to the first probe, each probe having a sealed internal chamber containing a pressurized fluid, wherein the fluid contained in each chamber of each probe is pressurized to a fluid pressure different than the fluid pressure in the other probe chambers.

5. An apparatus in accordance with claim 4, wherein each probe is a cylindrical tube having sidewalls and opposing, sealed ends, the tube and ends being made of the same material as the first material.

6. An apparatus in accordance with claim 3 wherein the sealed internal chamber of the second probe contains a fluid which is pressurized to a fluid pressure higher than that of said environmental pressure, but substantially lower than the fluid pressure in the chamber of the first probe.

7. An apparatus in accordance with claim 6, wherein the fluid in the chambers is a liquid.

8. An apparatus in accordance with claim 6, wherein the fluid in the chambers is a gas.

9. An apparatus in accordance with claim 5, wherein each probe is a cylindrical tube having sidewalls and opposing, sealed ends, the tube and ends being made of the same material as the first material.

10. An apparatus in accordance with claim 9, wherein the thicknesses of the sidewalls and ends of the first probe are different than the thicknesses of the sidewalls and ends of the second probe.

11. An apparatus in accordance with claim 9, wherein the fluid pressure in the first probe applies a stress to a portion of the probe, the stress being at least as high as 70% of the yield stress of the probe material.

12. A method of monitoring the corrosion of a first material exposed to a chemical environment having an environmental pressure, the method comprising:

(a) pressurizing a fluid contained in a sealed internal chamber of a first probe to a first fluid pressure, the first probe being made of a material substantially similar to the first material;

(b) pressurizing a fluid contained in a sealed internal chamber of a second probe to a second fluid pressure, said second pressure different from the first pressure, and the second probe being made of a material substantially similar to the first material;

(c) exposing the first and second probes to said environment; and (d) monitoring the fluid pressure within at least one of the chambers.

13. A method in accordance with claim 12 wherein the step of pressurizing the fluid in the chamber of the first probe further comprises pressurizing the fluid to a pressure substantially higher than said environmental pressure.

14. A method in accordance with claim 13 wherein the step of pressurizing the fluid in the chamber of the second probe further comprises pressurizing the fluid to a fluid pressure higher than said environmental pressure but substantially lower than the fluid pressure in the chamber of the first probe.

15. A method in accordance with claim 14, wherein the step of monitoring the fluid pressure within at least one of the chambers comprises connecting a pressure transducer in communication with at least one of the chambers.

* * * * *